(12) United States Patent
Diamant et al.

(10) Patent No.: US 10,925,624 B2
(45) Date of Patent: Feb. 23, 2021

(54) MEDICAL DEVICE FOR ENTRAPPING AND EXTRACTING OBJECTS FROM BODY CAVITIES

(71) Applicant: Nordson Corporation, Westlake, OH (US)

(72) Inventors: Valery Diamant, Katzrin (IL); Gennady Chepovetsky, Halutz (IL); Igor Gutman, Katzrin (IL); Alexandra Vainshtein, Katzrin (IL); Yuri Skopin, Katzrin (IL)

(73) Assignee: Nordson Corporation, Westlake, OH (US)

( * ) Notice: Subject to any disclaimer, the term of this patent is extended or adjusted under 35 U.S.C. 154(b) by 53 days.

(21) Appl. No.: 15/055,902

(22) Filed: Feb. 29, 2016

(65) Prior Publication Data
US 2017/0245873 A1    Aug. 31, 2017

(51) Int. Cl.
*A61B 17/221* (2006.01)
*A61B 17/22* (2006.01)
(Continued)

(52) U.S. Cl.
CPC ............ *A61B 17/221* (2013.01); *A61B 17/22* (2013.01); *A61F 2/013* (2013.01);
(Continued)

(58) Field of Classification Search
CPC ...... A61F 2/01; A61F 2/013; A61F 2002/016; A61B 17/221; A61B 2017/00867; A61B 2017/22038; A61B 2017/2212
See application file for complete search history.

(56) References Cited

U.S. PATENT DOCUMENTS

| 7,553,314 B2 | 6/2009 | Khachin et al. |
| 7,640,952 B2 | 1/2010 | Khachin et al. |
(Continued)

FOREIGN PATENT DOCUMENTS

| EP | 1574169 A2 | 9/2005 |
| EP | 1583477 B1 | 7/2009 |
(Continued)

OTHER PUBLICATIONS

Extended European Search Report dated May 31, 2017 in corresponding European Application No. EP16206968.6.

*Primary Examiner* — Kathleen S Holwerda
*Assistant Examiner* — Brooke Labranche
(74) *Attorney, Agent, or Firm* — BakerHostetler

(57) ABSTRACT

A retrieval medical device for entrapping and retaining an object located in a body for its extraction therefrom is described. The device includes a basket-filter constituted by a plurality of filaments extending from the proximal end towards the distal end. The filaments are bound together in the vicinity of the proximal end to form a plurality of main branches. Each main branch includes at least two filaments. The filaments are entangled together in the vicinity of the distal end. Each main branch has a ramification point at which it ramifies into at least two single filaments extending from the ramification point towards the basket distal end of the basket-filter. One of the single filaments extends in the form of a right spiral, whereas another single filament extends in the form of a left spiral. The filaments extending from the ramification points interlace with each other, thereby forming a mesh between the branching point and the basket proximal end having density greater than 5.1 crossover points per inch.

17 Claims, 6 Drawing Sheets

(51) Int. Cl.
*A61F 2/01* (2006.01)
*A61B 17/00* (2006.01)

(52) U.S. Cl.
CPC ........... *A61B 2017/00867* (2013.01); *A61B 2017/2212* (2013.01); *A61B 2017/22038* (2013.01); *A61F 2002/016* (2013.01); *A61F 2210/00* (2013.01)

(56) References Cited

U.S. PATENT DOCUMENTS

| | | |
|---|---|---|
| 9,039,715 B2 | 5/2015 | Diamant et al. |
| 9,271,746 B2 | 3/2016 | Diamant et al. |
| 2002/0045916 A1 | 4/2002 | William et al. |
| 2011/0082490 A1* | 4/2011 | Connelly .................. A61F 2/95 606/194 |
| 2015/0164522 A1 | 6/2015 | Tantra et al. |
| 2016/0058538 A1* | 3/2016 | Paul ......................... A61F 2/01 606/200 |

FOREIGN PATENT DOCUMENTS

| | | |
|---|---|---|
| RU | 2445025 C2 | 3/2012 |
| WO | 2004/056275 A1 | 7/2004 |
| WO | 2011/045916 A1 | 9/2011 |
| WO | 2014/087245 A2 | 6/2014 |

\* cited by examiner

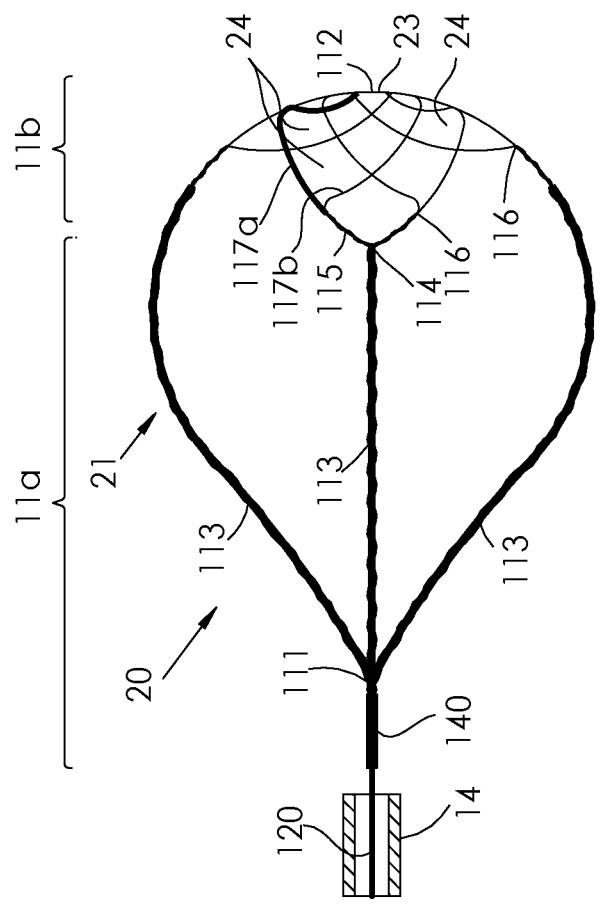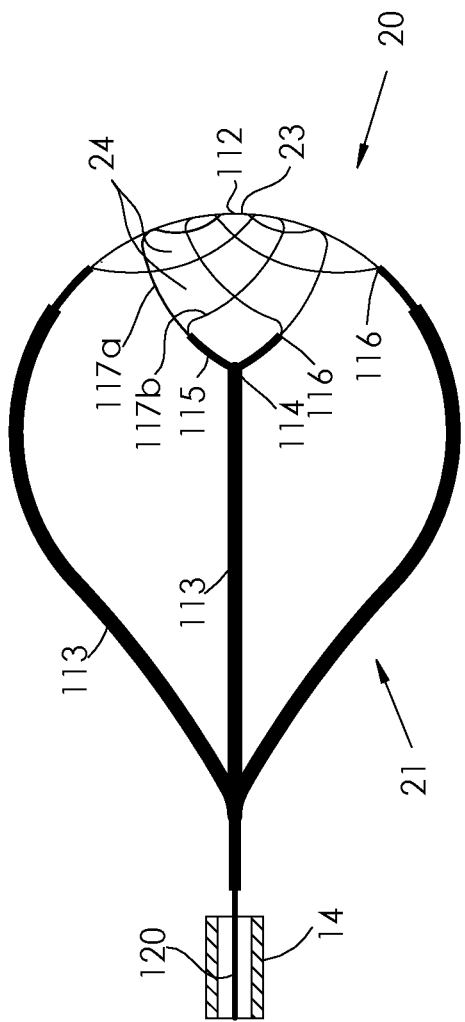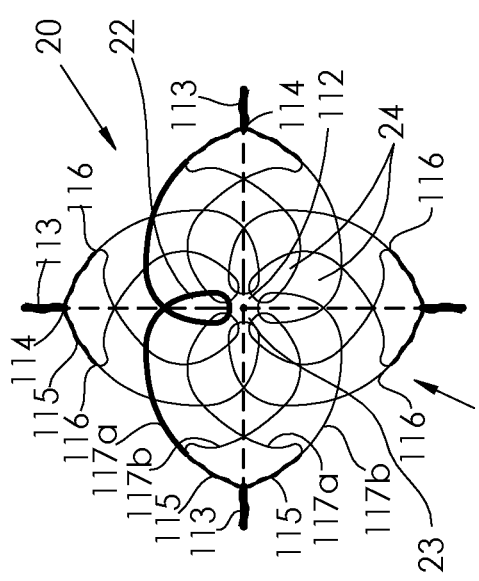

MEDICAL DEVICE FOR ENTRAPPING AND EXTRACTING OBJECTS FROM BODY CAVITIES

TECHNOLOGICAL FIELD

The present invention relates to an extraction device capable of capturing and extracting objects from hollow bodies, and in particular, to a medical instrument for entrapping and removing an object from a body.

BACKGROUND

Various instruments are known in the art for entrapping and removing various objects from the body. For example, such instruments are used for entrapping and removal of stones such as kidney stones, gallstones, and the like from various sites along the urinary tract of a patient's body. Likewise, such instruments can also be used in urology during a lithotripsy procedure in order to prevent migration of small fragments of broken stone from the ureter into the kidney, because such fragments can later serve as an embryo to form new concrements.

In addition to therapeutic drugs, minimally invasive devices are used that allow destruction of a thrombus. In this case, one must be careful that small particles (blood clots) of the disintegrated thrombus are not carried by the blood flow. Thus, a filter can be required to catch blood clots during the destruction procedure in order to entrap them. A retrieval device can further be used in order to safely remove them from the body.

Entrapping and retrieval devices are also widely used for removing foreign objects from the vascular system of a patient. For example, a detached blood clot (thromboembolism) that travels through the bloodstream and lodges can obstruct and/or occlude a blood vessel. In such a case, embolic protection devices, such as filters, extractors, vena cava filters and others similar devices are designed to successfully detain hardened pieces with different cardio procedures, without allowing them to migrate into the bloodstream, and in the future, allowing the practitioner to remove them from the body.

Extraction device instruments can employ a retrieval collapsible wire basket arranged within a flexible catheter formed as a tubular sheath adapted to penetrate body passages to reach the location from where the object is to be evacuated (see, for example U.S. Pat. Nos. 7,553,314 and 7,640,952 to Khachin et. al.). The basket and the sheath can move relative to each other to open and close the basket. The basket includes flexible wires and is made of a material capable to provide the basket with elasticity. The wires are bound together in the vicinity of a basket proximal end as well as at a basket distal end. Depending on the manipulation, the basket may either retract inside the sheath, to allow penetration of the catheter via a passage, or protract from the catheter. In the protracted position, the basket is open, due to the elasticity of the wire material, and forms a cage to thus allow entrance of the object into the basket through the open spaces left between its adjacent wires. Further retraction of the basket into the sheath results in the cage collapsing and entrapping the object in the basket. Removal of the catheter will enable the whole device to be removed from the body organ together with the object immobilized within the basket. During an operation, the operator moves the catheter behind the object to be extracted, and then protracts the basket from the catheter. Once the basket is protracted, it opens (due to its resiliency), and is ready for receiving the object to be entrapped therein. The operator pulls the catheter together with the basket until it entraps the object, and then extracts the entrapped object from the body.

General Description

There is a need to provide a convenient and safe entrapping and retrieval apparatus suitable for reliable and efficient entrapping and extraction of objects from body tracts and hollow organs. It would also be advantageous to have an entrapping and retrieval apparatus that can be universal, in order to be used both in urology in order to entrap and retain relatively large and hard objects such as kidney stones, gallstones or their fragments; and in different cardio procedures, in order to entrap and remove relatively soft objects such as soft blood clots, thrombus clots, occlusions, and relatively small calcinated plaques.

It would be advantageous to have a retrieval device that has relatively small dimensions in the undeployed state so it may be easily inserted into the body through known guiding catheters, and then can allow entrapping and removal of relatively large clots/objects, by deployment to a larger dimension.

It would also be advantageous to have a device that can simultaneously perform the functions of a basket and a filter, i.e. to catch and hold small fragments of various objects, preventing their distribution in hollow organs. The present invention satisfies the aforementioned need by providing a medical basket-filter retrieval device suitable for entrapping and retaining an object located in a body for its extraction therefrom. The entrapping and retrieval device includes a basket-filter and a basket control assembly. The basket-filter can change its configuration between a deployed state and contracted state and includes a structure having a proximal section and a distal section interconnected to each other. It should be noted that in the description and claims that follow, the terms "proximal" and "distal" are used with reference to the operator of the device.

According to an embodiment of the present invention, the basket-filter has a proximal end arranged at the proximal section, and a distal end arranged at the distal section. The basket-filter is constituted by a plurality of filaments extending from the proximal end towards the distal end. The filaments are bound together in the vicinity of the proximal end to form a plurality of main branches. Each main branch includes at least two filaments. The filaments are entangled together in the vicinity of the distal end. Each main branch has a ramification point at which it ramifies into at least two single filaments extending from the ramification point towards the distal end of the basket-filter. One of the single filaments extending from the ramification point extends in the form of a right spiral, whereas another single filament of the two single filaments extends in the form of a left spiral. The filaments extending from the ramification points interlace with each other, thereby forming a mesh between the branching point and the basket proximal end.

According to an embodiment, the mesh has a density along a longitudinal axis greater than about 5.1 crossover points per inch (PPI) (i.e. about 2 crossover points per centimeter), where a crossover point is the place, where filaments intersect (interlace or overlap). Such density of the mesh is required in order to catch and entrap foreign objects larger than 5 mm in size. Objects having smaller dimensions than 5 mm are considered to be less harmful for the patient, and therefore may be left in the body.

According to an embodiment of the present invention, each main branch ramifies at the ramification point into two sub-branches. Each sub-branch includes half of the filaments of the corresponding main branch and has a sub-branch ramification point at which it ramifies the two single filaments that extend in the form of the left spiral and the right spiral, correspondingly.

According to an embodiment, the two single filaments that extend in the form of the left and right spirals make at least one full turn.

According to an embodiment, the filaments in the vicinity of the distal end are connected together to form a basket-filter tip at the distal end. When desired, the connected filaments can extend outward from the basket-filter tip to form a guide wire.

According to one embodiment, the filaments in each main branch and in each sub-branch are bound together by twisting together.

According to another embodiment, the filaments in each main branch and in each sub-branch are directly bound together by at least one technique selected from soldering, brazing and gluing.

According to yet an embodiment, the filaments in each main branch and in each sub-branch are bound together by tubes placed over the filaments.

According to some embodiments, each single filament extending from the corresponding ramification point towards the distal end of the basket-filter bends in the vicinity of the distal end, and returns to the other ramification point to form a loop. At the distal end, each loop is entangled with two other loops formed by two other filaments to define a distal opening at the distal end.

According to some embodiments, each single filament extending from the corresponding sub-branch ramification point towards the distal end of the basket-filter bends in the vicinity of the distal end, and returns to the other sub-branch ramification point, thereby forming a loop. At the distal end, each loop is entangled with two other loops formed by two other filaments to define a distal opening at the distal end.

According to some embodiments, each single filament extending from the corresponding ramification point towards the distal end of the basket-filter bends in the vicinity of the distal end, and returns to the same ramification point from which said single filament originates to form a loop. At the distal end, each loop is entangled with two other loops formed by two other filaments, thereby defining a distal opening at the distal end.

According to some embodiments, the medical device includes a control assembly. The control assembly includes a delivery catheter and a manipulation member coupled to the filter-basket. The delivery catheter has a lumen, and is configured to penetrate into the body for reaching the object. The manipulation member is configured to path within the lumen of the delivery catheter, and to operate for (i) protracting the basket-filter from the delivery catheter for opening thereof and (ii) retracting the basket-filter within the delivery catheter for collapsing the basket-filter inside of the delivery catheter.

According to some embodiments, the manipulation member includes at least a part of the plurality of filaments extending from the proximal end of the basket-filter.

According to some embodiments, the manipulation member includes a pushing tube containing at least a part of the plurality of filaments axially disposed within the lumen of the pushing tube along at least a portion of the tube's length.

According to some embodiments, the filaments are made of metallic material. Preferably, but not mandatory, the metallic material has thermo-mechanical shape memory and superelastic characteristics.

According to some embodiments, the filaments are made of non-metallic material.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIGS. 2A and 2B illustrate a top view and a cross-sectional plan view, respectively, of the distal part of a basket-filter device in a deployed position for entrapping and retaining an object, according to a further embodiment of the present invention;

FIG. 2C illustrates a cross-sectional plan view of the distal part of a basket-filter device, according to yet another embodiment of the present invention;

DETAILED DESCRIPTION OF EMBODIMENTS

Figure 1A:
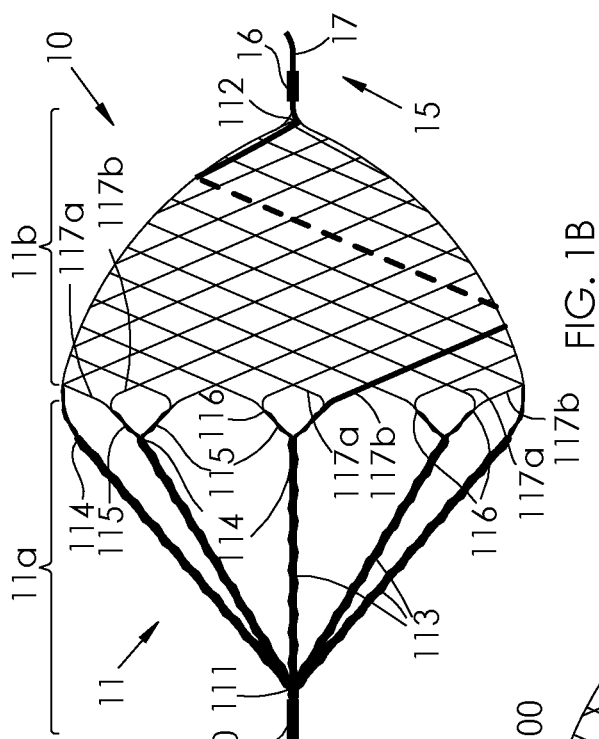
FIGS. 1A and 1B illustrate a top view and a cross-sectional plan view, respectively, of a distal portion of a medical basket-filter device in a deployed position for entrapping and retaining an object, according to one embodiment of the present invention.

The principles of construction and operation of the medical device according to the present invention may be better understood with reference to the drawings and the accompanying description, wherein like reference numerals have been used throughout to designate identical elements, it being understood that these drawings which are not necessarily to scale, are given for illustrative purposes only and are not intended to limit the scope of the invention. Examples of constructions, materials, dimensions, and manufacturing processes are provided for selected elements. Those versed in the art should appreciate that many of the examples provided have suitable alternatives which may be utilized.

Embodiments of the present invention generally provide a medical entrapping and retrieval basket-filter device that includes generally an entrapping and retrieval basket-filter having a parachute type and include a structure with a mesh at a distal part of the device, and a control assembly coupled to the structure. The control assembly includes a delivery catheter configured to penetrate into the body for reaching the object; and a manipulation member coupled to the basket-filter. The manipulation member is configured to path within the delivery catheter and to operate for (i) protracting the basket-filter from the delivery catheter for opening the basket-filter, and (ii) retracting the basket-filter within the delivery catheter for collapsing the retrieval device inside of the delivery catheter.

Figure 1B:
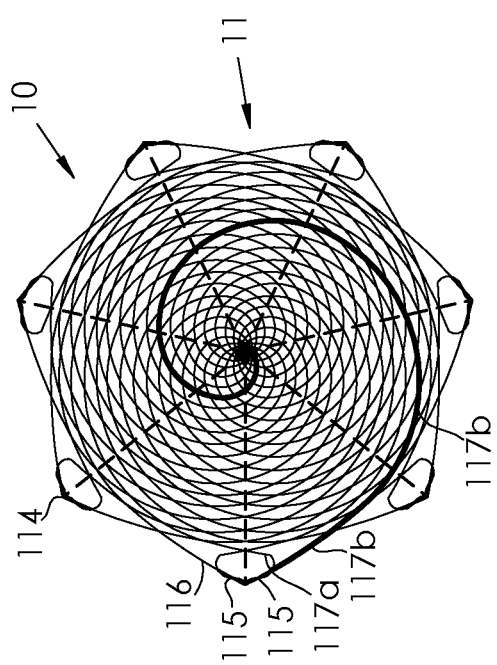

FIGS. 1A and 1B illustrate a view top and a cross-sectional plan view, respectively, of the distal part of a retrieval device 10 equipped with the basket-filter 11 (shown in a deployed position) for entrapping and retaining an object (not shown), and a control assembly 12 coupled to the basket-filter 11, according to one embodiment of the present invention. The control assembly 12 includes a manipulation member 120 coupled to a proximal end 111 of the basket-filter 11, as will be described in detail hereinbelow, and a delivery catheter 14. The deployed (open) state of the basket-filter 11 is achieved when the basket-filter is located outside of the delivery catheter 14.

In practice, the operator moves the delivery catheter 14 behind the object to be extracted, and then protracts the basket-filter 11 from the catheter 14. Once the basket-filter is protracted, it opens due to its resiliency and is ready for receiving the object to be entrapped therein. The operator pulls the manipulation member 120 until the basket-filter 11 entraps the object, and then extracts the entrapped object from the body.

The delivery catheter 14 is a thin-walled, cylindrical deflectable tube fabricated of a relatively stiff yet somewhat pliant material, which operates as a sheath and permits the apparatus to be introduced into a patient's body along a tortuous path for reaching an object. For example, the delivery catheter 14 can be made of polymeric material, such as polyimide, polyvinyl chloride, NYLON, TEFLON, etc. The delivery catheter 14 can also be made of metal or composite materials. For example, it can be made in the form of a coil, (e.g., stainless steel coil) or a metal tube. Likewise, it can be a braided reinforced plastic tube. When desired, the sheath 14 may be multi-layered with different materials in order to provide a graduated bending and stiffness characteristic over its length.

The structure of the basket-filter 11 has a proximal section 11a and a distal section 11b, and is formed by a plurality of filaments that extend from the proximal end 111 of the basket-filter 11 located at the proximal section 11a towards a distal end 112 of the basket-filter 11 located at the distal section 11b. The filaments are bound together in the proximal section 11a in the vicinity of the proximal end 111 to form a plurality of main branches 113. In the embodiment shown in FIGS. 1A and 1B, the basket-filter 11 has seven branches; however, other configurations with different numbers of the main branches are also contemplated.

Figure 1C:
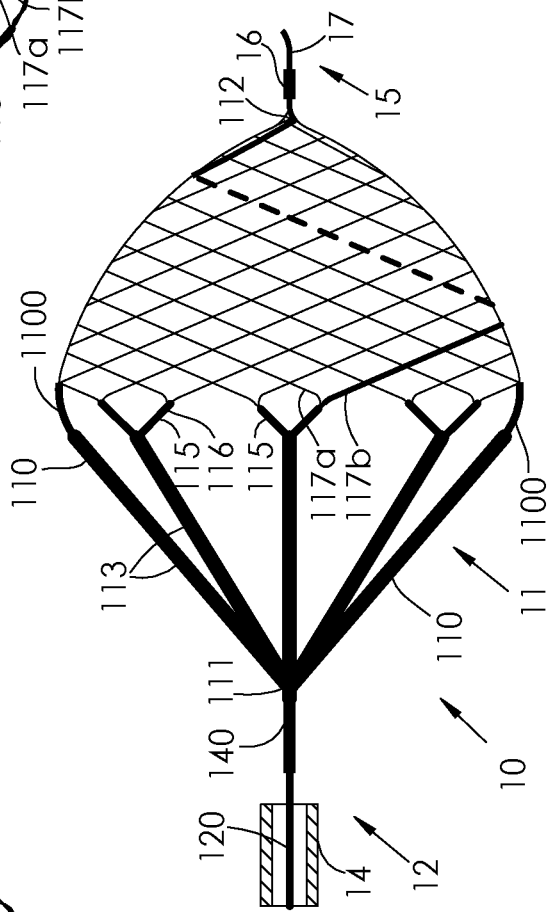
FIG. 1C illustrates a cross-sectional plan view of the distal part of a 1 basket-filter device, according to another embodiment of the present invention.

As shown in FIG. 1B, in proximal section 11a, the filaments in each main branch 113 are bound together by twisting together to form strands. However, when desired, the filaments in each main branch 113 can be directly bound together along their length by any other suitable technique, such as by soldering, brazing, gluing, etc. Likewise, as shown in FIG. 1C, the filaments in each main branch 113 can be bound together by tubes 110 placed over the filaments. This provision can increase mechanical strength of the branches, and accordingly increase mechanical strength of the entire structure of the basket filter 11. The tubes 110 can be made of thermo-shrinkable material.

Each main branch 113 includes a plurality of filaments associated in one or more pairs of filaments. According to the embodiment shown in FIGS. 1A-1C, each main branch 113 includes two filament pairs, i.e. four filaments. All the filaments originated from the proximal end 111 are entangled together at the distal end 112.

According to the embodiment shown in FIGS. 1A-1C, each main branch 113 has a ramification point 114 at which it ramifies into two sub-branches 115. Each sub-branch 115 includes half of the filaments of the corresponding main branch 114, i.e. two filaments.

In the deployed state, the proximal section 11a of the basket-filter 11 has relatively large openings left between the adjacent branches. By virtue of these openings, the catching of an object (not shown) within the body and immobilization thereof inside the proximal section 11a becomes easy and convenient during the catching stage of the treatment, when the basket-filter 11 catches and entraps blood clots or stones in a blood vessel or in an ureter, correspondingly, for a further retrieval. Likewise, catching of an object can be carried out when the operator begins pulling the basket-filter 11 for entrapping the object.

As shown in FIG. 1B, the filaments in each sub-branch 115 are also bound together by twisting together to form strands. However, when desired, the filaments in each sub-branch 115 can also be directly bound together by any other suitable technique, such as by soldering, brazing, gluing, etc. Likewise, as shown in FIG. 1C, the filaments in each sub-branch 115 can be bound together by tubes 1100 placed over the filaments.

Each sub-branch 115 has a sub-branch ramification point 116 at which it ramifies into two single filaments 117a and 117b. The filament 117a extends from the sub-branch ramification point 116 in the distal section 11b in the form of the left spiral, whereas the filament and 117b extends from the sub-branch ramification point 116 in the form of the right spiral, correspondingly. For clarity of illustration of the spiral formed by the filaments, one of the filaments 117b is shown by a bold line. As shown in FIGS. 1A-1C, the single filaments 117a and 117b that extend in the form of the left and right spirals make at least one full turn, however other configurations are also contemplated.

The filaments 117a and 117b extending from sub-branch ramification points 116 interlace and can partially overlap with each other in the distal section 11b, thereby forming a mesh between the sub-branch ramification points 116 and the basket proximal end 112. Note that the term "overlap" herein is broadly used to describe such arrangement of the filaments, in which one element crosses other filaments, i.e., one of the filaments always being over or under several other filaments. The term "interlace" herein is broadly used to describe the situation when at least one filament interweaves with the other filaments, i.e., the filament passes first above a certain crossed filament and then passes under the next crossed filament.

While the drawings show the mesh on an enlarged scale, a particular advantage of this structure is its ability to provide a mesh of relatively small and compact construction. Such a construction can be achieved due to the spiral configuration of the interlaced filaments 117a and 117b. The retention ability of the basket-filter 11 depends on the size the mesh cells that depend on density of the mesh (defined by number of crossover points per centimeter or per inch), which, in turn, depends on the number of the main branches and on the number of the turns in the left and right spirals formed by the filaments 117a and 117b. The maximum value of the density corresponds to the case when the neighboring filaments are attached to each other and the size of the mesh cells is minimal, and depends on the diameter of the filament wires. For example, filaments of the retrieval basket-filter 11 can each have a cross-sectional diameter in the range of about 0.05 mm to about 0.3 mm.

According to an embodiment, the mesh has a density along a longitudinal axis greater than about 5.1 crossover points per inch (PPI) (i.e. about 2 crossover points per centimeter), where a crossover point is the place, where filaments intersect (interlace or overlap). Such value of the density is much more than in the prior art basket structures heretofore known. The meshes having such density are required in order to catch and entrap foreign objects larger than 5 mm in size. Objects having smaller dimensions than 5 mm are considered to be less harmful for the patient, and therefore may be left in the body. It should be understood that when the mesh density is greater than 5.1 PPI, concrements having dimensions smaller than 5 mm can be entrapped. For example, when the density is 6.4 PPI, concrements having dimensions of 4 mm and larger can be entrapped.

According to an embodiment of the present invention, the filaments in the vicinity of the distal end 112 are connected together to form a basket-filter tip 15 at the distal end 12. As shown in FIGS. 1A-1C, the filaments in the vicinity of the distal end 112 are connected by a bushing 16, however the connection can be carried out by twisting, soldering, brazing, gluing and/or by any other suitable technique. When desired, the connected filaments can extend outward from the basket-filter tip 15 to form a guide wire 17. The guide wire 17 can function as a guide to facilitate penetration and movement of the whole medical device 10 within the body organs.

FIG. 2A shows a top view and FIGS. 2B and 2C show a cross-sectional plan view of the distal part of a retrieval device 20 equipped with a basket-filter 21 (shown in a deployed position) for entrapping and retaining an object (not shown), according to a further embodiment of the present invention. The basket-filter 21 differs from the basket-filter 11 in the fact that the basket-filter 21 has four main branches 113, and the single filaments 117a and 117b extending from the corresponding sub-branch ramification point 116 of the sub-branch branch 115 towards the distal end 112 of the basket-filter, bend in the vicinity of the distal end 112, and then return after winding to the other sub-branch ramification point 116 of the other sub-branch 115 to form a loop 22. For clarity of illustration of the loops formed by the filaments, the filament 117a is shown by a bold line.

As shown in FIG. 2B, in the proximal section 11a, the filaments in each main branch 113 and each sub-branch 115 are bound together by twisting together. However, when desired, the filaments in each main branch 113 and in each sub-branch 115 can also be directly bound together by any other suitable technique, such as by soldering, brazing, gluing, etc. Likewise, as shown in FIG. 2C, the filaments in each main branch 113 and in each sub-branch 115 can be bound together by tubes 110 and 1100, correspondingly, placed over the filaments.

In the distal section 11b of the basket-filter shown in FIGS. 2A-2C, the filaments forming the loops are interlaced with each other so as to form a mesh that has a distal opening 23 at the distal end 112, and a plurality of side openings 24 along the lateral part of the mesh structure.

Figure 3:
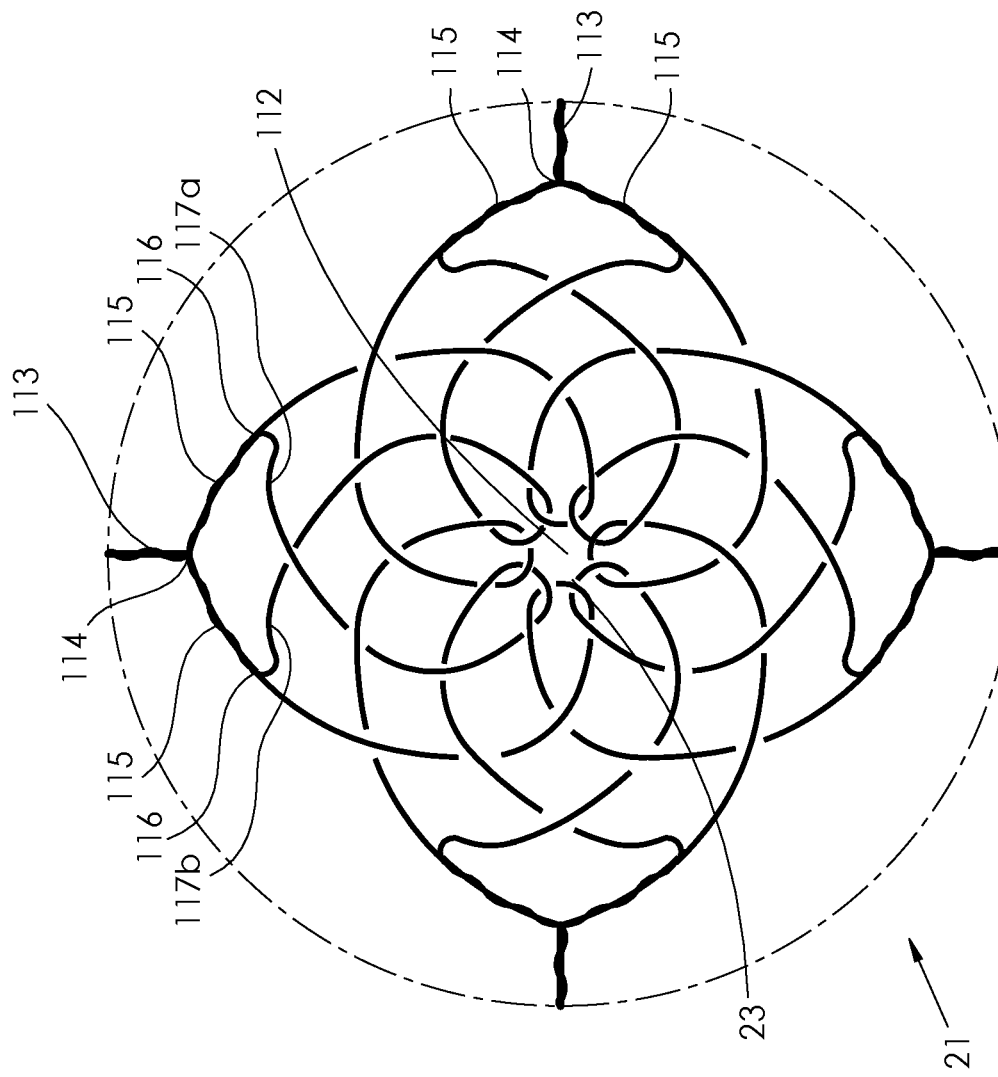
FIG. 3 illustrates the configuration of the interlaced filaments in the basket-filter shown in FIGS. 2A-2C in detail.

FIG. 3 illustrates a configuration of the interlaced filaments in the filter-basket 21 shown in FIGS. 2A-2C in detail. Each filament that originates from a certain branch interlaces with a plurality of the filaments which originate from all other branches. The distal opening 23 is formed by the entangled filaments that change their direction at the distal end 112 to form loops. Each loop that is formed by a filament which originated from a certain branch is entangled with two other loops formed by two other filaments which originated from two other branches. Thus, a small and compact construction of the medical device can be obtained with the density of the mesh greater than 5.1 PPI crossover points per inch.

Figure 4:
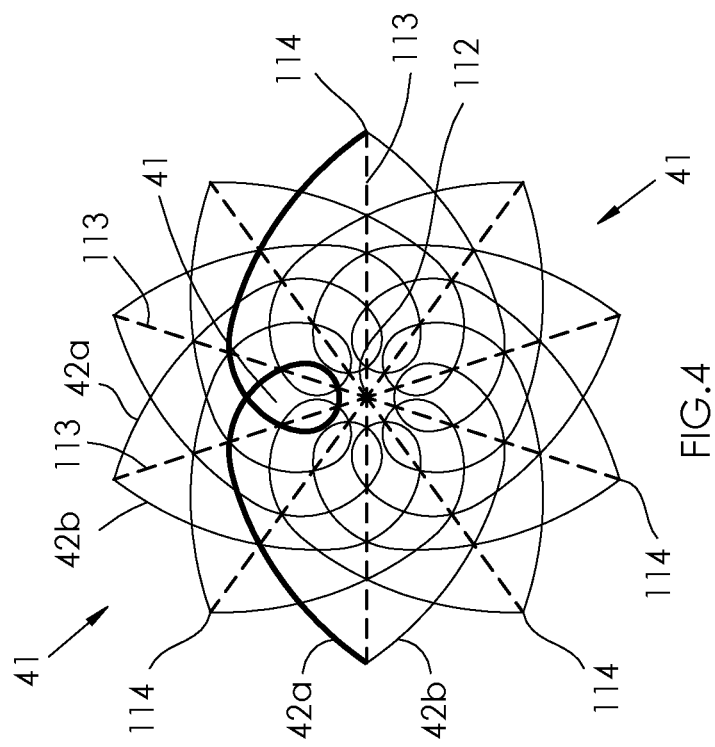

The number of the main branches 113 may be different. FIG. 4 shows a top view of the distal section of a basket-filter 41 (shown in a deployed position) for entrapping and retaining an object (not shown), according to yet another embodiment of the present invention. The basket-filter 41 has ten main branches 113, which are shown by dotted lines in FIG. 4. The basket-filter 41 differs from the basket-filter (21 in FIG. 3) in the fact that the basket-filter 41 does not have sub-branches. Single filaments 42a and 42b extend from the corresponding ramification points 114 of the main branch 113 towards the distal end 112 of the basket-filter, bend in the vicinity of the distal end 112, and then return after winding to the other ramification point 114 of the other main branch 113 to form a loop 41. For clarity of illustration of the loops formed by the filaments, one of the filaments 42a forming a loop is shown by a bold line.

Figure 5:
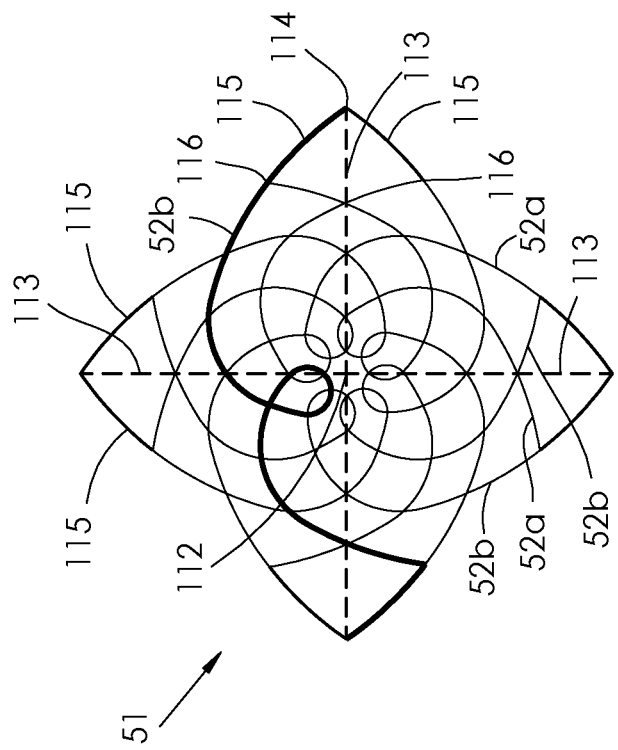
FIGS. 4 and 5 illustrate a top view of the distal part of a basket-filter that has four main branches, according to two different embodiments of the invention.

According to the embodiment shown in FIGS. 2A-2C, 3, each filament that originates from the sub-branch ramification point 116 of a certain sub-branch 115 in the form of the right spiral arrives to the sub-branch ramification point 116 of other sub-branch 115 as the filament which is in the form of the left spiral, however other configurations of the filaments are also contemplated. For example, FIG. 5 illustrates a configuration of the interlaced and/or overlapped filaments in a basket-filter 51 that differs from the configuration shown in FIGS. 2A-2C and 3 in the fact that each filament 52a that originates from the sub-branch ramification point 116 of a certain sub-branch 115 in the form of the left spiral arrives to a sub-branch ramification point 116 of another sub-branch 115 as the filament which is also in the form of the left spiral.

Figure 7:
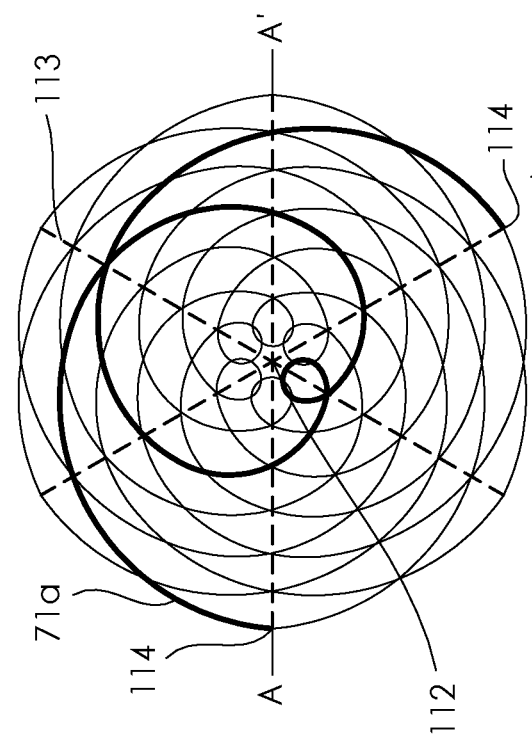
FIGS. 6-8 illustrate a top view of the distal part of a basket-filter that has six main branches, according to three different embodiments of the invention.
Figure 6:
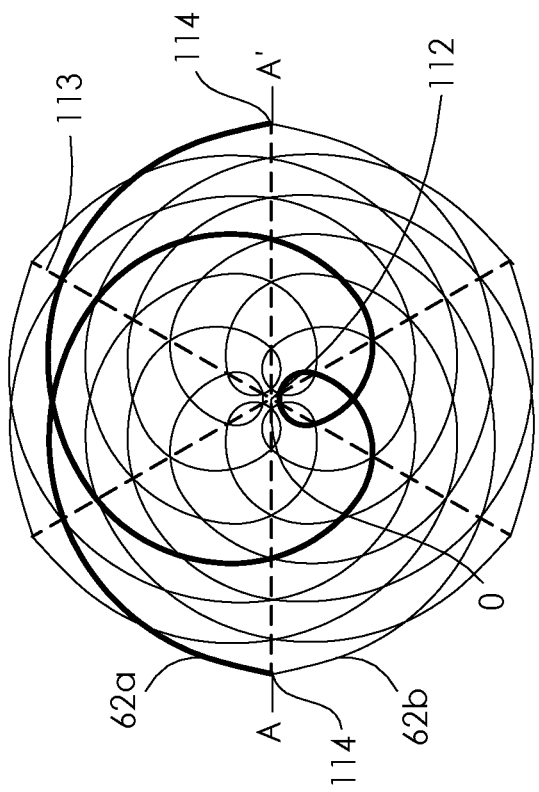
Figure 8:
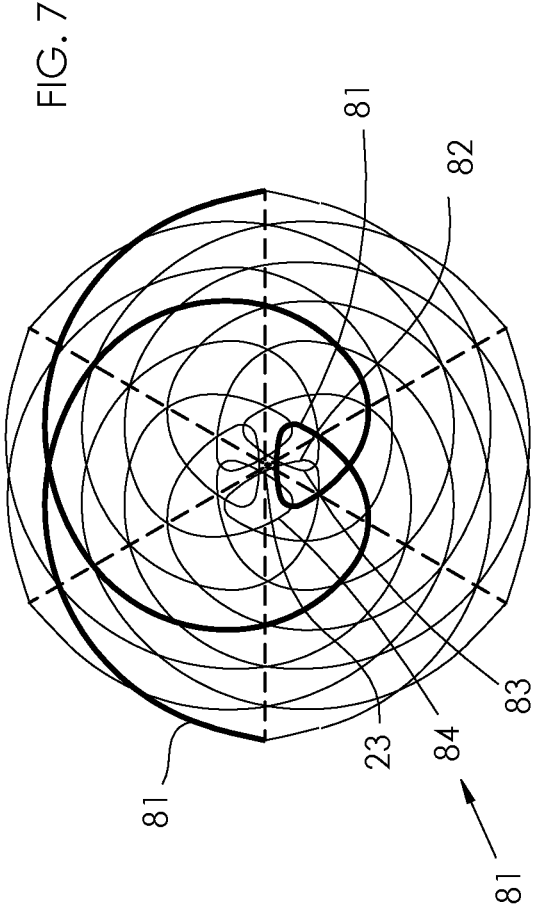

FIGS. 6-8 illustrate three different embodiments of the configuration of the interlaced filaments in the mesh of basket-filters 61, 71 and 81 that has six main branches 113. The basket-filters 61, 71 and 81 do not have sub-branches. As shown in FIG. 6, the single filaments 62a and 62b extend from the corresponding ramification points 114 of a certain main branch 113 (shown by dotted lines) towards the distal end 112 of the basket-filter, bend in the vicinity of the distal end 112, and then return after winding to the other ramification point 114 of the other main branch 113 to form a loop. For clarity of illustration of the loops formed by the filaments, one of the filaments 62a forming a loop is shown by a bold line. As shown in FIG. 6, the filaments 62a originate from the branching point 114 of a certain branch 113 and arrive to the branching point 114 of another branch, which is located at the opposite side of the basket-filter 61 along a diametrical axis A-A' of the basket-filter 61.

The embodiment shown in FIG. 7 differs from the embodiment shown in FIG. 6 in the fact that the branching points 114 from which a filament (shown by a bold line 71a) originate and the branching points 114 to which it arrives after forming a loop are not located on the diametrical axis A-A'.

FIG. 8 illustrates an embodiment in which, near the distal opening 23, each filament 81 forming a loop is overlapped with filaments 82 and 83 and is interlaced with filaments 84 and 85.

Each filament of the basket filter described above is a single-core wire. However, when desired, each filament can be a multi-wire strand or multi-core wire. The filaments utilized for the fabrication of the basket-filter 11 are made of a suitable material that is suitably biocompatible and has thermo-mechanical shape memory and/or superelastic properties. According to one embodiment of the invention, the filaments are made of a metallic material. For example, the metallic material can be selected from a group including a NiTi based alloy (e.g., Nitinol), stainless steel and other materials possessing good shape memory, elastic or superelastic characteristics. According to another embodiment of the invention, the filaments are made of non-metallic material, for example Capron, Nylon, etc.

According to a still further embodiment of the invention, the filaments of the basket-filter are covered by an insulating layer. The insulating layer can, for example, be made of Teflon. The advantage of Teflon is its thermal resistance and low coefficient of mechanical friction, which leads to an additional reduction of traumatism.

According to a still further embodiment of the invention, the filaments of the basket-filter can be covered by hydrophilic coating which also provides a value of the friction coefficient.

A preferable, but not mandatory feature is, the filaments being radiopaque, so as to permit them to be visualized by a fluoroscope with respect to the object to be retracted. Thus, according to one example, radiopacity may be provided by the metallic material from which the filaments are made and may include a material which provides radiopacity, for example a noble metal, such as gold, tantalum, platinum, etc. Likewise, the metallic material can be alloyed with one or more of the following metals: Pd, W, Nb, Co, and Cu.

According to another example, the filaments are made of a core tube (cannular strand) containing an axially disposed radiopaque wire, for example, a radiopaque core clad with a different outer material. Examples of radiopaque materials include Pt, Au, Pd, W, Nb, Co, Ta, Ag, and Cu without limitation. Examples of cladding materials include stainless steel, Nitinol, and polymers such as Capron and Nylon without limitation.

According to yet another example, the filaments can have radiopaque parts of a predetermined length. These radiopaque parts can form the distal section 11b of the basket-filter device or at least a part of the distal section.

Radiopacity can also be improved through coating processes such as sputtering or plating a radiopaque material onto the filaments, or the basket-filter being fabricated from these filaments, thereby to provide a radiopaque coating layer on the filaments.

Likewise, radiopacity can yet be improved by using radiopaque markers (not shown), which can be attached to or placed around the filaments forming the basket-filter. In this manner, materials, which have higher radiopacity than the basket-filter structure itself, such as gold, tantalum or platinum, can be utilized as markers and be strategically placed along the body of the basket-filter to increase the visualization of the basket-filter. For example, the basket-filter 11 can comprise one or more radiopaque markers (not shown) attached to or placed around the filaments in the distal section 11b. For example, the radiopaque marker can be a ferrule placed on the filament.

According to another embodiment of the invention, the filaments can be multi-wire strands. In such a case, in order to improve radiopacity, the multi-wire strands can include a central core wire and at least one another wire twisted about the central core wire which is made of a material having a level of radiopacity greater than the level of radiopacity of the central core wire. Examples of such a material include, but are not limited to, Pt, Au, Pd, Ag, Ta, etc.

Referring to FIGS. 1A through 2C together, the filaments are bound together at the proximal end 111 of the basket-filter 11. According to an embodiment of the invention, the filaments are bound together by a ferrule 140 crimped or swaged together with the filaments at the proximal end 111. The filaments that extend from the ferrule 140 can be bound together, for example, by twisting together. Thus, these twisted filaments can possess sufficient stiffness in order to form or be a part of a manipulation member 120 of the retrieval device.

The manipulation member 120 is arranged within the delivery catheter 14 and is operable for retracting the basket-filter 11 within the delivery catheter 14 and protracting the delivery catheter therefrom for its opening. The manipulation member 120 connects the basket-filter 11 to a manipulator (not shown) that is operable for manipulating the basket-filter 11 for extraction of foreign objects from the body. When desired, the manipulation member 120 can be formed from at least a part of the plurality of filaments extending from the proximal end 111 towards the manipulator.

In practice, an operator of the medical device can manipulate the manipulation member 120 by means of the manipulator, and thus the basket-filer can be either retracted within the catheter 14 or protracted therefrom. The operator, by holding the manipulator, can also maneuver the catheter 14 within the body organ (not shown), (e.g. to displace it by turning, pushing or pulling).

Figure 9:
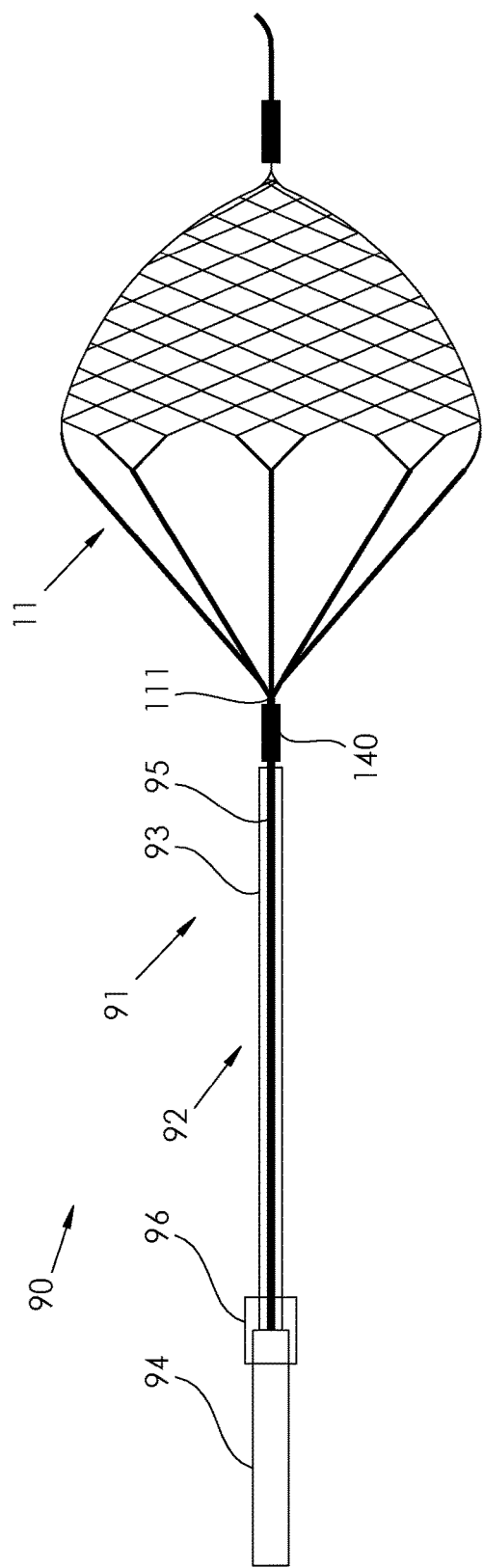
FIG. 9 illustrates a schematic view of connection of the basket-filter to a manipulation member, according to one embodiment of the invention.

Referring to FIG. 9, a basket-filter device 90 is shown which includes the basket filter and the control assembly 91. Although the basket-filter 11 that is shown in FIG. 1C is shown in FIG. 9, it should be understood that the basket-filter may be any one of the embodiments described above. The control assembly 91 includes a manipulation member 92 having a pushing tube 93 and a manipulator 94 connected to the tube 93. At least a part of the filaments forming the basket-filter are bound together at the proximal end 111 by a ferrule 140 and extend further from the end 111 towards the manipulator 94. These filaments 95 are axially disposed within a lumen of the pushing tube 93 along at least a portion of the tube's length. When desired, the filaments 95 can be twisted together to provide additional rigidity to the manipulation member 94.

The pushing tube 93 and the filaments 95 can be bound together. For example, the tube 93 and the filaments 95 can be crimped, swaged, glued, soldered or welded together. When desired, to increase the surface area binding the filaments to the tube, the tube 93 can have one or more notches (not shown) through which a glue or soldering material can be delivered.

In some embodiments, the tube 93 may be disposed within catheter sheath (not shown in FIG. 9) as described above.

As shown in FIG. 9, the tube 93 may be arranged between the ferrule 140 and the manipulator 94, as shown in FIG. 9.

Alternatively, the tube 93 can bind together the filaments at the end 111 of the proximal section 111A of the basket-filter, essentially functioning as the ferrule 140, and thereby allowing the ferrule 140 to be omitted.

The tube 93 can, for example, be made of a metallic material selected from a NiTi based alloy, or stainless steel. Likewise, the tube 93 can be made of a polymer material or braided reinforced polymeric materials. According to the embodiment shown in FIG. 9, the manipulation member 92 is connected to the manipulator 94 through a ferrule 96 placed and crimped around the tube 93 and the manipulator 94.

According to another embodiment, the manipulation member 92 can be directly connected to the manipulator 94, omitting the ferrule 65. The manipulator 94 can, for example, have a cannular end. Thus, it can be put on the tube 93, and connected to the tube by a gluing, soldering and/or welding process.

To increase the binding surface, the manipulator 94 can be provided with one or more notches (not shown) through which a glue or soldering material can be delivered.

Figure 10:
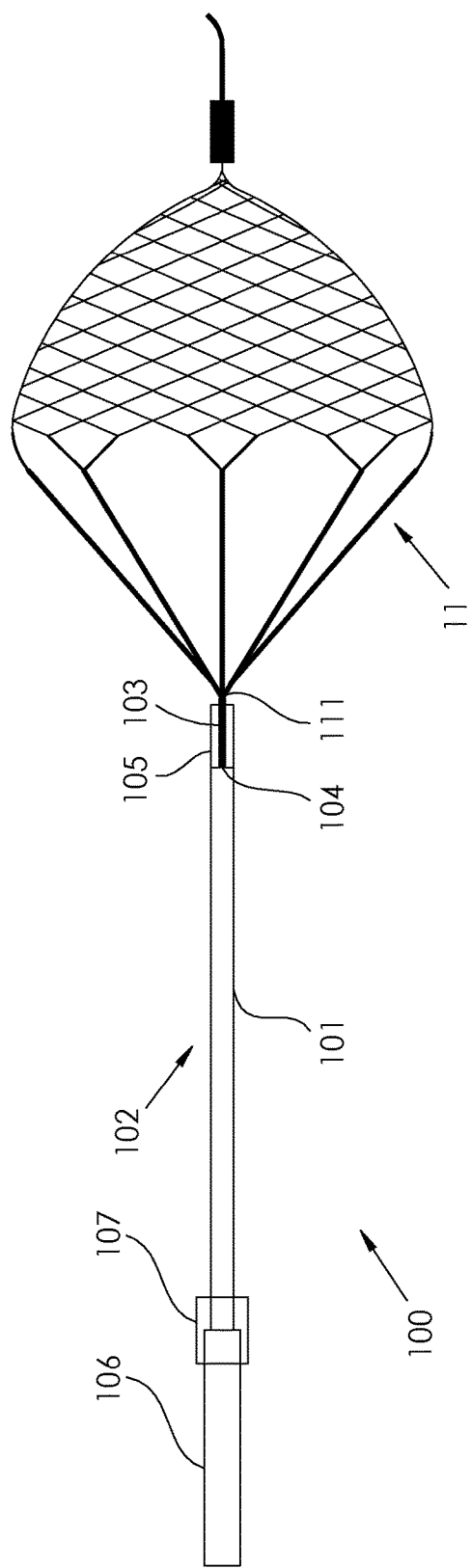
FIG. 10 illustrates a schematic view of connection of the basket-filter to a manipulation member, according to another embodiment of the invention.

Referring to FIG. 10, a schematic view of connection of a basket-filter 11 to a pushing tube 101 in order to form a manipulation member 102 of the retrieval apparatus 100 is shown, according to another embodiment of the present invention. Although the basket-filter that is shown in FIG. 1C is shown in FIG. 10, it should be understood that the basket-filter may be any one of the embodiments described above.

As shown in FIG. 10, at least a part of the filaments 103 which are extended from the proximal end 111 are cut off at a predetermined distance from the end, thereby forming free filament ends 104. These free filament ends 104 are placed in a lumen of the pushing tube 101 and are crimped or welded together at a portion 105, thereby to form a manipulation member. The pushing tube 101 of this manipulation member can be connected to a manipulator 106, for example, by using a ferrule 106 that is placed and crimped around the pushing tube 101 and the manipulator 106.

According to another example, the pushing tube 101 of the manipulation member 102 can be directly connected to the manipulator 106 omitting the ferrule 106. Thus, the manipulator 106 can be put on the pushing tube 101 and connected thereto by a gluing, soldering and/or welding process. As discussed above, the manipulator 106 can be provided with one or more notches (not shown) through which a glue or soldering material can be delivered to increase the binding surface area.

In some embodiments, the tube 101 may be disposed within catheter sheath (not shown in FIG. 10), as described above.

From the foregoing description it should be appreciated that a basket-filter retrieval device constructed in accordance with the present invention can comprise a variety of user desired shapes, a number of filaments forming branches and a mesh, types of connection of the filaments in the proximal portion and types of connection of the filaments to a manipulation member. The filaments may be bound at the distal portion to form a tip as well as be bent at the distal end, returning to the proximal end to form loops.

Generally, any desired number of the loops may be employed, provided that density of the mesh is greater than 5.1 crossover points per inch (PPI). Such density of the mesh is required in order to catch and entrap foreign objects larger than 5 mm in size. Objects having smaller dimensions than 5 mm are considered to be less harmful for the patient, and therefore may be left in the body. It should be understood that when the mesh density is greater than 5.1 PPI, concrements having dimensions smaller than 5 mm can be entrapped. For example, when the density is 6.4 PPI, concrements having dimensions of 4 mm and larger can be entrapped.

As such, those skilled in the art to which the present invention pertains, can appreciate that while the present invention has been described in terms of preferred embodiments, the concept upon which this disclosure is based may readily be utilized as a basis for the designing of other structures and processes for carrying out the several purposes of the present invention.

It should be understood that the basket-filter of the present invention is not limited to medical treatment of a human body. It can be successfully employed for medical treatments of animals as well. Furthermore, the device of the invention is suitable for retrieval of objects from various hollow organs and cavities in body systems, for example, from blood vessels, the urinary tract, etc.

Moreover, the present invention is not limited to fabrication of medical devices, thus the retrieval apparatus of the invention can be used to catch and extract any type of article from a wide range of inaccessible locations such as inside a pipe or tube (for example, the waste outlet of a domestic sink) or inside a chamber within a large piece of machinery which would be difficult to dismantle.

Also, it is to be understood that the phraseology and terminology employed herein are for the purpose of description and should not be regarded as limiting.

It is important, therefore, that the scope of the invention is not construed as being limited by the illustrative embodiments set forth herein. Other variations are possible within the scope of the present invention as defined in the appended claims and their equivalents.

The invention claimed is:

1. A medical device for entrapping and retaining an object located in a body for its extraction therefrom, the medical device comprising:
   a basket-filter having a proximal end and a distal end, the basket-filter being constituted by a plurality of filaments extending from the proximal end towards the distal end,
       wherein the plurality of filaments are bound together in the vicinity of the proximal end to form a plurality of main branches, each main branch having at least two filaments, the at least two filaments being entangled together in the vicinity of the distal end,
       wherein each main branch includes a ramification point at which said main branch ramifies into at least two single filaments extending from the ramification point towards the distal end of the basket-filter, the basket-filter defining a proximal section between the proximal end and the ramification point and a distal section between the ramification point and the distal end,
       wherein one of the at least two single filaments extends in the form of a right spiral, whereas another of said at least two single filaments extends in the form of a left spiral,
       wherein the at least two single filaments extending from the ramification points interlace with each other, thereby forming a distal mesh in the distal section between the ramification points and the distal end, the distal mesh having a density of between about 5.1 crossover points per inch to about 6.4 crossover points per inch, the distal mesh configured to entrap an object greater than 4 mm in size within the basket-filter,
       wherein each of the at least two single filaments extend from a corresponding ramification point towards the distal end of the basket-filter, bends in a vicinity of the distal end, and returns to one of the corresponding ramification point and another ramification point to form a loop,
       wherein at the distal end, each loop formed from each of the at least two single filaments is entangled with at least another loop formed by another of the at least two single filaments such that the loops together define a distal opening at a distal-most point of the distal end, the distal opening being coaxial to a longitudinal axis extending through the basket-filter from the proximal end to the distal-most point of the distal end, wherein the density of the distal mesh increases from the proximal end to the distal end, and wherein the filaments in the proximal section define a proximal mesh configured to permit an object greater than 4 mm in size to pass therethrough, the proximal mesh having a density less than about 5.1 crossover points per inch.

2. The medical device of claim 1, wherein each of the at least two filaments extending from the corresponding ramification point towards the distal end of the basket-filter bends in the vicinity of the distal end, and returns to another ramification point to form the loop.

3. The medical device of claim 1, further comprising a control assembly comprising:
a delivery catheter having at least one lumen, and configured to penetrate into the body for reaching the object; and
a manipulation member coupled to the basket-filter, and configured to path within said at least one lumen of the delivery catheter, and to operate for (i) protracting the basket-filter from the delivery catheter for opening thereof and (ii) retracting the basket-filter within the delivery catheter for collapsing the basket-filter inside of the delivery catheter.

4. The medical device of claim 3, wherein the manipulation member includes at least a part of the plurality of filaments extending from the proximal end of the basket-filter.

5. The medical device of claim 3, wherein the manipulation member includes a pushing tube containing at least a part of the plurality of filaments axially disposed within a lumen of the pushing tube along at least a portion of the tube's length.

6. The medical device of claim 1, wherein the plurality of filaments are made of metallic material or a non-metallic material.

7. The medical device of claim 6, wherein the metallic material has thermos-mechanical shape memory and super-elastic characteristics.

8. The medical device of claim 1, wherein openings defined by the mesh of the basket-filter decreases from the proximal end towards the distal end.

9. The medical device of claim 1, wherein the basket-filter includes between 16 and 24 filaments.

10. The medical device of claim 9, wherein each of the plurality of filaments has a cross-sectional diameter of about 0.05 mm to about 0.3 mm.

11. A medical device for entrapping and retaining an object located in a body for its extraction therefrom, the medical device comprising:
a basket-filter having a proximal end and a distal end, the basket-filter being constituted by a plurality of filaments extending from the proximal end towards the distal end,
wherein the plurality of filaments are bound together in the vicinity of the proximal end to form a plurality of main branches, each main branch having at least two filaments, the at least two filaments being entangled together in the vicinity of the distal end,
wherein each main branch includes a ramification point at which said main branch ramifies into at least two single filaments extending from the ramification point towards the distal end of the basket-filter, the basket-filter defining a proximal section between the proximal end and the ramification point and a distal section between the ramification point and the distal end, wherein one of the at least two single filaments extends in the form of a right spiral, whereas another of said at least two single filaments extends in the form of a left spiral, wherein the at least two single filaments extending from the ramification points interlace with each other, thereby forming a distal mesh in the distal section between the ramification points and the distal end, the distal mesh having a density of between about 5.1 crossover points per inch to about 6.4 crossover points per inch, the distal mesh configured to entrap an object greater than 4 mm in size within the basket-filter, wherein each of the at least two single filaments extend from a corresponding ramification point towards the distal end of the basket-filter, bends in a vicinity of the distal end, and returns to one of the corresponding ramification point and another ramification point to form a loop, wherein at the distal end, each loop formed from each of the at least two single filaments is entangled with at least another loop formed by another of the at least two single filaments such that the loops together define a distal opening at the distal end, wherein the density of the distal mesh increases from the proximal end to the distal end, wherein the filaments in the proximal section define a proximal mesh configured to permit an object greater than 4 mm in size to pass therethrough, the proximal mesh having a density less than about 5.1 crossover points per inch, wherein each main branch ramifies at the ramification point into two sub-branches, each sub-branch includes half of the filaments of the corresponding main branch and has a sub-branch ramification point at which said sub-branch ramifies into said at least two single filaments that extend in the form of the left spiral and the right spiral, correspondingly, and wherein each of the at least two single filaments extend from the corresponding sub-branch ramification point towards the distal end of the basket-filter, bends in the vicinity of the distal end, and returns to another sub-branch ramification point, thereby forming the loop.

12. The medical device of claim 11, wherein said at least two single filaments that extend in the form of the left and right spirals make at least one full turn.

13. The medical device of claim 11, wherein the filaments in each main branch and in each sub-branch are bound together by twisting together.

14. The medical device of claim 11, wherein the filaments in each main branch and in each sub-branch are directly bound together by at least one technique selected from soldering, brazing and gluing.

15. The medical device of claim 11, wherein the filaments in each main branch and in each sub-branch are bound together by tubes placed over the filaments.

16. A medical device for entrapping and retaining an object located in a body for its extraction therefrom, the medical device comprising:

a basket-filter having a proximal end and a distal end, the basket-filter being constituted by a plurality of filaments extending from the proximal end towards the distal end,
- wherein the plurality of filaments are bound together in the vicinity of the proximal end to form a plurality of main branches, each main branch having at least two filaments, the at least two filaments being entangled together in the vicinity of the distal end,
- wherein each main branch includes a ramification point at which said main branch ramifies into at least two single filaments extending from the ramification point towards the distal end of the basket-filter, the basket-filter defining a proximal section between the proximal end and the ramification point and a distal section between the ramification point and the distal end,
- wherein one of the at least two single filaments extends in the form of a right spiral, whereas another of said at least two single filaments extends in the form of a left spiral,
- wherein the at least two single filaments extending from the ramification points interlace with each other, thereby forming a distal mesh in the distal section between the ramification points and the distal end, the distal mesh having a density of between about 5.1 crossover points per inch to about 6.4 crossover points per inch, the distal mesh configured to entrap an object greater than 4 mm in size within the basket-filter,
- wherein each of the at least two single filaments extend from a corresponding ramification point towards the distal end of the basket-filter, bends in a vicinity of the distal end, and returns to one of the corresponding ramification point and another ramification point to form a loop,
- wherein at the distal end, each loop formed from each of the at least two single filaments is entangled with at least another loop formed by another of the at least two single filaments such that the loops together define a distal opening at the distal end,
- wherein the density of the distal mesh increases from the proximal end to the distal end,
- wherein the filaments in the proximal section define a proximal mesh configured to permit an object greater than 4 mm in size to pass therethrough, the proximal mesh having a density less than about 5.1 crossover points per inch, and
- wherein said at least two single filaments that extend in the form of the left and right spirals make at least two full turns.

17. A medical device for entrapping and retaining an object located in a body for its extraction therefrom, the medical device comprising:

a basket-filter having a proximal end and a distal end, the basket-filter being constituted by a plurality of filaments extending from the proximal end towards the distal end,
- wherein the plurality of filaments are bound together in the vicinity of the proximal end to form a plurality of main branches, each main branch having at least two filaments, the at least two filaments being entangled together in the vicinity of the distal end,
- wherein each main branch includes a ramification point at which said main branch ramifies into at least two single filaments extending from the ramification point towards the distal end of the basket-filter, the basket-filter defining a proximal section between the proximal end and the ramification point and a distal section between the ramification point and the distal end,
- wherein one of the at least two single filaments extends in the form of a right spiral, whereas another of said at least two single filaments extends in the form of a left spiral,
- wherein the at least two single filaments extending from the ramification points interlace with each other, thereby forming a distal mesh in the distal section between the ramification points and the distal end, the distal mesh having a density of between about 5.1 crossover points per inch to about 6.4 crossover points per inch, the distal mesh configured to entrap an object greater than 4 mm in size within the basket-filter,
- wherein each of the at least two single filaments extend from a corresponding ramification point towards the distal end of the basket-filter, bends in a vicinity of the distal end, and returns to one of the corresponding ramification point and another ramification point to form a loop,
- wherein at the distal end, each loop formed from each of the at least two single filaments is entangled with at least another loop formed by others of the at least two single filaments such that the loops together define a distal opening at the distal end,
- wherein the density of the distal mesh increases from the proximal end to the distal end,
- wherein the filaments in the proximal section define a proximal mesh configured to permit an object greater than 4 mm in size to pass therethrough, the proximal mesh having a density less than about 5.1 crossover points per inch, and
- wherein the distal opening at the distal end is bounded by all of the loops formed from each of the at least two single filaments.

* * * * *